US006190377B1

United States Patent
Kuzdrall (12) United States Patent
(10) Patent No.: US 6,190,377 B1
(45) Date of Patent: Feb. 20, 2001

(54) METHOD AND APPARATUS FOR PREDICTIVE BEAM ENERGY CONTROL IN LASER SURGERY

(76) Inventor: James A. Kuzdrall, 103 Linwood St., Nashua, NH (US) 03060

(*) Notice: Under 35 U.S.C. 154(b), the term of this patent shall be extended for 0 days.

(21) Appl. No.: 09/305,656

(22) Filed: May 5, 1999

(51) Int. Cl.$^7$ .................................................. A61B 18/18
(52) U.S. Cl. .................................. 606/10; 606/9; 607/89
(58) Field of Search .................................. 606/10–12, 9, 606/49, 159; 607/88, 89, 96

(56) References Cited

U.S. PATENT DOCUMENTS

| | | | |
|---|---|---|---|
| 5,599,342 | * 2/1997 | Hsia et al. | 606/9 |
| 5,662,644 | * 9/1997 | Swor | 606/9 |
| 5,707,403 | * 1/1998 | Grove et al. | 607/89 |
| 5,879,376 | * 3/1999 | Miller | 607/89 |
| 6,027,495 | * 2/2000 | Miller | 606/9 |
| 6,083,217 | * 7/2000 | Tankovich | 606/9 |

* cited by examiner

Primary Examiner—Linda C. M. Dvorak
Assistant Examiner—Ahmed Farah
(74) Attorney, Agent, or Firm—Aquilino, Welsh & Flaxman, P.C.

(57) ABSTRACT

A method and apparatus is disclosed for predicting an effective and safe laser light energy range for sub-epidermal laser surgery. The method is especially useful in controlling beam energy during the treatment of PWS. The method is accomplished by first impinging a measurement laser pulse on a predetermined treatment area, wherein the measurement laser pulse has an energy below a predetermined threshold of coagulation and below a predetermined threshold of skin damage. The thermal emission caused by the measurement laser pulse emanating from the treatment area is then detected and the delay time from the measurement laser pulse to the detection of the thermal emission is measured. The rise rate of the thermal emission is then measured. The layer thickness is then calculated based upon the delay time, wherein the layer thickness is substantially the epidermal thickness. An internal measurement temperature rise is calculated based upon the layer thickness and the rise rate. Finally, the energy of the measurement laser pulse is multiplied by a minimum scaling ratio to obtain a minimum laser treatment energy, wherein the minimum scaling ratio is the known coagulation temperature divided by the internal measurement temperature rise, and the energy of the measurement laser pulse is multiplied by a maximum scaling ratio to obtain a maximum laser treatment energy, wherein the maximum scaling ratio is the known skin damage threshold temperature divided by the measurement temperature rise.

15 Claims, 4 Drawing Sheets

METHOD AND APPARATUS FOR PREDICTIVE BEAM ENERGY CONTROL IN LASER SURGERY

BACKGROUND OF THE INVENTION

1. Field of the Invention

This invention relates generally to measurement methods and specifically to controllers for laser surgery.

2. Discussion of Prior Art

Malformed blood vessels just beneath the skin surface cause skin disorders such as birthmarks, spider veins, rosacea, and hemangenomas. These disorders respond to treatment by an intense pulse of laser radiation.

For example, a birthmark known as "Port Wine Stain" (PWS), named for its appearance, is one specific disorder that is treated with a laser radiation pulse. These blemishes appear at infancy as pink areas, usually on the face and neck, but darken to purplish red during childhood.

PWS occurs when an abnormally high concentration of blood vessels forms in the papillary and reticular layer of derma, just beneath the two outer skin layers, the statum corneum and stratum Malpighii, collectively identified with the epidermis. The epidermis is typically 0.1 millimeters thick in a typical laser treatment area, while the interlocking projections of the papillary dermis range from 0.5 to 0.9 millimeters thick.

Thus, the blood vessels targeted for treatment typically lie 0.6 to 1.0 millimeters below the skin surface in young facial skin.

A visible yellow wavelength, 585 nanometers, is the accepted optimum choice for the treatment laser. This wavelength traverses the epidermis with relatively little absorption, but is highly absorbed by the blood vessels. In effect, the outer skin layer acts like a slightly milky pane of glass with dark blood vessels pressed against its underside.

When laser treatment is applied to a predetermined skin site, the intense beam of laser light passes through the skin to the blood vessel layer. The laser beam energy is absorbed when it reaches the blood vessels. The absorbed energy heats the blood and vessels to such high temperatures that they coagulate, or "cook".

After treatment, a normal body function, lymphatic transport, removes the lifeless material. The body then heals, rebuilding the destroyed oversized vessels with normal sized vessels. When the healing process is complete, the properly treated skin has normal blood vessels, permanently removing the PWS birthmark.

The outer skin layer remains intact throughout the laser treatment and protects the underlying tissue. With this normal body defense in place, there is no risk of infection. Because the laser interaction takes place beneath the intact outer skin, the treatment is referred to as sub-epidermal laser surgery.

Prior to the development of the present invention, damage to the dermal and epidermal layers posed a difficult problem in PWS and related laser surgeries. Specifically, if the laser beam is too intense, heat from the coagulating blood vessels "cooks" the adjacent outer skin layers. Once the protective layers are destroyed, the treatment area becomes an open wound, inviting infection. Furthermore, the damaged surface often forms scar tissue on healing. As a result, laser surgery may remove the PWS, but a disfiguring scar replaces the PWS. The patient must then either endure skin graft surgery or live with the scar, depending on medical practicalities.

The skin surface destruction occurs because, prior to the present invention, there was no practical way to predict the necessary laser energy (intensity) required to properly treat PWS. Physicians generally set the laser beam energy, and hence the coagulating heat, based on personal experience. Consequently, some patients receive too much laser energy causing scars, some receive too little laser energy causing no improvement in the PWS condition, and others receive the correct amount and are cured.

One experimental guidance aid uses a Computer Aided Tomographic (CAT) image to improve PWS treatment. However, CAT images are expensive and difficult to employ. Specifically, acquiring the CAT data requires a very expensive infrared imaging camera; processing the image for tomographic display takes several minutes on a premium desktop personal computer; and calculations must be repeated for each 4 square millimeters of treated skin area.

The CAT image provides the physician with a picture of the underlying tissue, but offers no guidance for the desired laser energy settings. Thus, the CAT approach proves both expensive and slow, while leaving the physician to guess at an energy setting based simply on a picture of the underlying tissue.

After considering the prior art systems employed in the laser treatment of PWS and other disorders, it is clear that a convenient and reliable technique is needed by those afflicted with PWS and those treating the disorder. The present invention provides a beam energy control system overcoming the shortcomings of prior art techniques.

SUMMARY OF THE INVENTION

Accordingly, it is an object of this invention to provide a method and apparatus for predicting the allowed range of laser energy settings for effective therapy of PWS, and other disorders treated with laser surgery, at each treatment location. The allowed range extends from a minimum laser treatment energy, which is just sufficient to coagulate, to a maximum laser treatment energy, which is just below the threshold of skin damage.

It is also an object of the present invention to provide a method and apparatus for predicting an effective and safe laser light energy range wherein calculations based on measured quantities advise the physician as to the energy bounds for safe and effective treatment.

It is a further object of the present invention to provide a method and apparatus for predicting an effective and safe laser light energy range wherein the energy bounds are specific to each treatment site.

It is another object of the present invention to provide a method and apparatus for predicting an effective and safe laser light energy range wherein the measured quantities are simple scalars (quantities completely described by a single number) rather than a matrix, vector field, tensor, pixel mapped image, or other complex data combination.

It is also an object of the present invention to provide a method and apparatus for predicting an effective and safe laser light energy range wherein the calculations require only 2 simple, scalar measured quantities.

It is another object of the present invention to provide a method and apparatus for predicting an effective and safe laser light energy range wherein the measured quantities can be obtained, if desired, from a simple, single element infrared detector rather than an expensive infrared camera.

It is a further object of the present invention to provide a method and apparatus for predicting an effective and safe laser light energy range wherein the energy bounds come from algorithms and formulae much simpler than those required for CAT images, thus allowing fast processing on computers of modest computing power.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

With reference to FIGS. 1 to 4, the present invention relates to a method and apparatus for controlling beam energy. In accordance with the invention, a low energy laser pulse creates a thermal emission at a laser surgery treatment site on a patient's skin. The measured delay time and rise rate of the thermal emission pulse allows calculation of the correct energy range for a subsequent high energy treatment pulse which safely coagulates the unwanted blood vessels.

More specifically, the present invention is a method and apparatus for predicting an effective and safe laser light energy range for sub-epidermal laser surgery. The method is especially useful in controlling beam energy during the treatment of PWS. The method is accomplished by first impinging a measurement laser pulse on a predetermined treatment area, wherein the measurement laser pulse has an energy below a predetermined threshold of coagulation and below a predetermined threshold of skin damage. The thermal emission caused by the measurement laser pulse emanating from the treatment area is then detected and the delay time from the measurement laser pulse to the detection of the thermal emission is measured. The rise rate of the thermal emission is then measured and the layer thickness is calculated based upon the delay time, wherein the layer thickness is substantially the epidermal thickness. An internal measurement temperature rise is calculated based upon the layer thickness and the rise rate. Finally, the energy of the measurement laser pulse is multiplied by a minimum scaling ratio to obtain a minimum laser treatment energy, wherein the minimum scaling ratio is the known coagulation temperature, approximately 50° C. divided by the internal measurement temperature rise, and the energy of the measurement laser pulse is multiplied by a maximum scaling ratio to obtain a maximum laser treatment energy, wherein the maximum scaling ratio is the known skin damage threshold temperature, approximately 90° C. divided by the measurement temperature rise.

Figure 1:
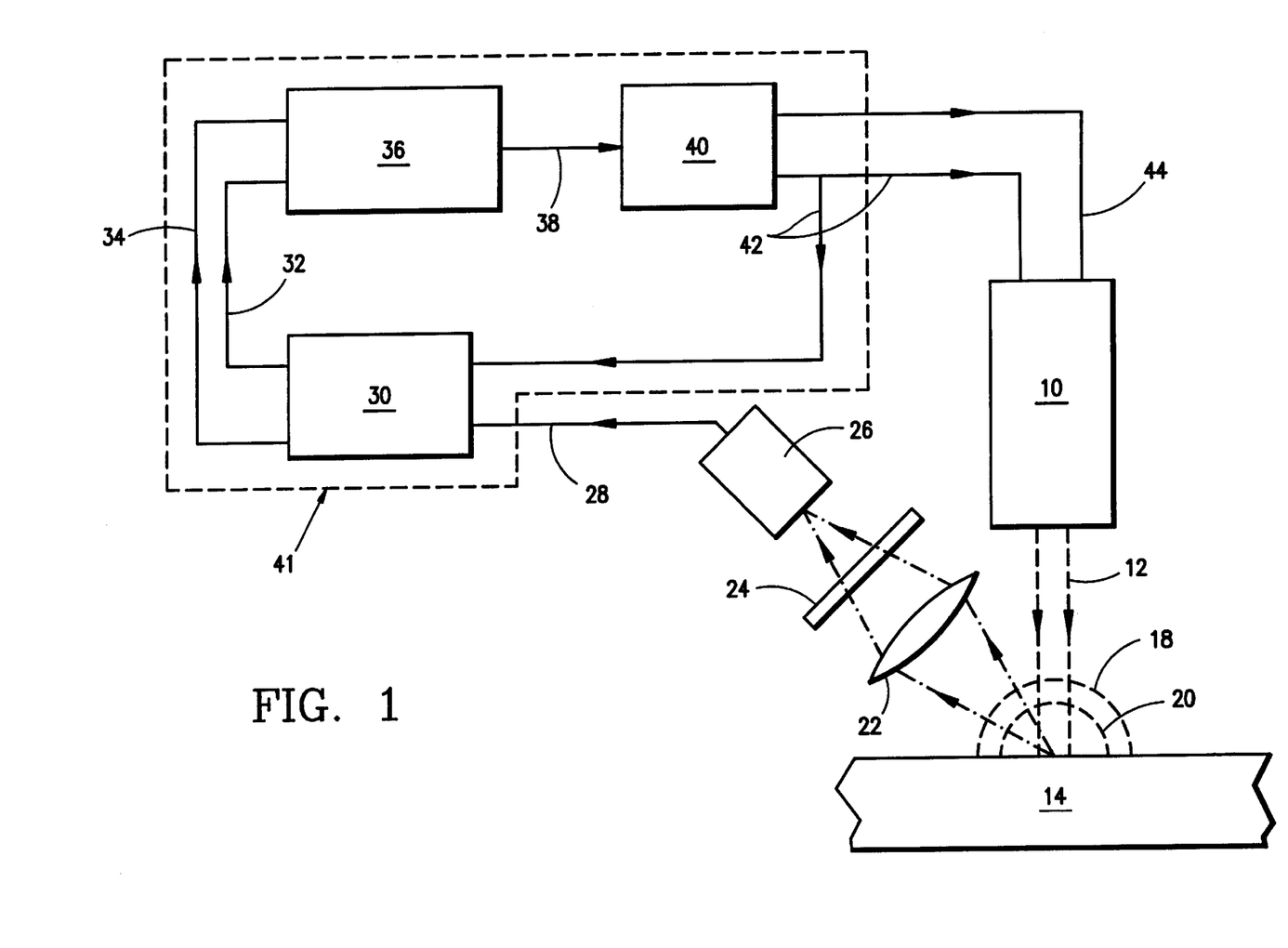
FIG. 1 is a schematic block diagram of the invention.

With reference to FIG. 1, an arrangement for a laser surgery controller implementing the present method and apparatus is depicted. A surgical laser 10 produces a collimated laser light beam 12. Typically, the laser 10 operates at wavelengths shorter than 2 microns (preferably 585 nanometers, a yellow hue), while thermal emissions occur in the 2 micron to 23 micron range for observed temperature rises. The wavelength of the laser 10 is preferably chosen to pass with minimal absorption through a translucent layer 82 (see FIG. 3A) of an individual's skin, but to be strongly absorbed by the underlying blood vessels. Those skilled in the art will, therefore, appreciate that operation of the present invention is not dependent on a specific laser wavelength or on the spectral ranges being separated. As such, various wavelengths and spectral ranges may be employed without departing from the spirit of the present invention.

Two control signals 42, 44 issued by a control console 40 regulate the operation of the laser 10. These signals are preferably electronic, although other signals, for example, pneumatic, mechanical, or any other type, may be employed without departing from the spirit of the present invention. Pneumatic or mechanical actuators are used where the laser intensity cannot be controlled electrically or if the electrical control range is not wide enough. Specifically, an on/off control signal 42 switches the beam 12 on and off, while an energy control signal 44 adjusts the energy of the beam 12.

The beam 12 impinges on a predetermined skin treatment site 14. In accordance with the preferred embodiment of the present invention, the site 14 is a portion of skin surface as shown in cross section. As the beam 12 hits the treatment site 14, a diffuse reflection 18 arises from the treatment site 14. Somewhat later, a thermal emission 20 arises from the treatment site 14. A radiant energy concentrator 22, typically a lens, gathers and focuses both the diffuse reflection 18 and the thermal emission 20.

The gathered energy from the concentrator 22 passes through a spectral filter 24. The spectral filter 24 blocks the diffuse reflection 18 and passes the thermal emission 20. In cases where the laser 10 operates at a wavelength within the thermal emission wavelength range, the spectral filter 24, preferably of a narrow blocking wavelength, removes the laser 10 light with negligible effect on the amplitude of the thermal emission 20. As those skilled in the art will readily appreciate, the spectral filter 24 is typically an inherent feature of the concentrator 22, although various components may be employed without departing from the spirit of the present invention.

An infrared detector 26 converts the thermal emission 20 to an electrical waveform signal 28. Typically, the infrared detector 26 inherently responds to the thermal emission 20, but not to the diffuse reflection 18.

A waveform processor 30 extracts a measured delay signal 32 and a measured rise rate signal 34 from the waveform signal 28. The measured delay signal 32 and measured rise rate signal 34 are typically extracted using the on/off control signal 42 as the reference for the delay.

A computer 36 converts the measured delay signal 32 and the measured rise rate signal 34 to an energy range signal 38. The control console 40 initiates pulses of laser light beam 12 based upon the calculated energy range signal 38. The control console 40 preferably includes a user interface which displays or otherwise communicates the bounds indicated by the energy range signal 38 for a physician to accept or modify.

As discussed below in greater detail, the control console 40 accepts manual initiation or semiautomatic initiation of the beam 12. The processor 30, computer 36, and control console 40 collectively comprise a signal processor assembly 41.

Upon initiation, the control console 40 sets the energy control signal 44 and activates the on/off control signal 42. Some suitable lasers combine energy control signal 44 and on/off control signal 42 by allowing the energy control signal 44 to be set at zero energy.

In practice, the present predictive beam energy controller generates two pulses of laser energy, a measurement pulse and a treatment pulse, at each treatment site 14. In manual operation, the attending physician initiates each pulse. The energy of the first pulse is low, intended for measurement only. The second pulse is high energy and produces the desired blood vessel coagulation.

Typically, the same laser and optics produce both the measurement pulse and treatment pulse. This arrangement inherently assures that the measurement occurs exactly at the treatment site, thereby ensuring that the energy bounds are specific to each treatment site.

Sequence Of Laser Pulse Events

Figure 2:
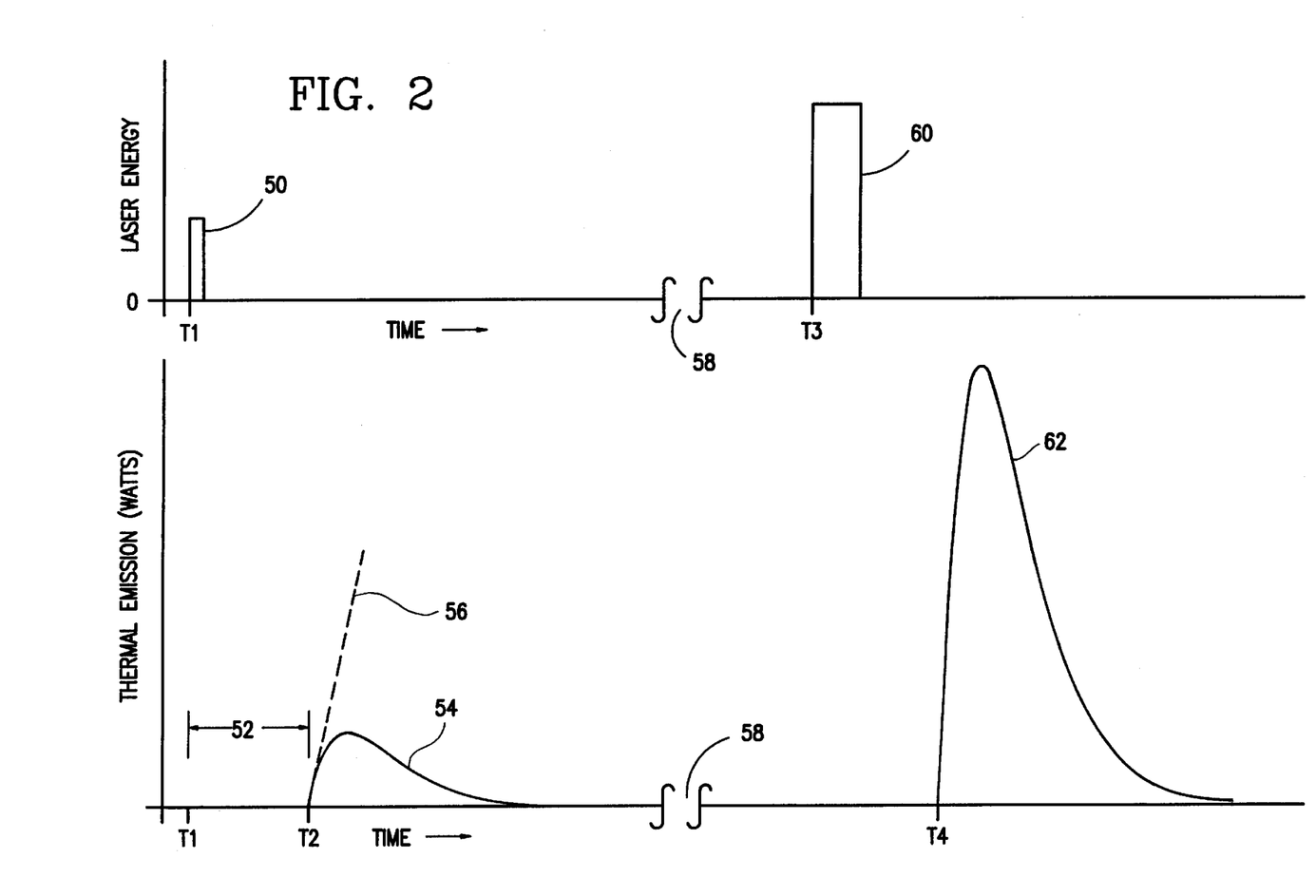
FIG. 2 shows the time and amplitude relationship of laser energy and thermal emission.

FIG. 2 shows a brief, low energy, laser measurement pulse 50, beginning at time T1. The duration of the measurement pulse 50 is typically less than 500 microseconds.

With reference to FIGS. 3A to 3E, a temporal sequence showing the spread of heat beneath the skin surface during the procedure embodied by the present invention is disclosed. A skin surface 80 marks the outer boundary of the skin. Directly within the skin surface 80, a translucent layer 82 comprises the stratum disjunctum, stratum corneum, stratum lucidum, stratum granulosum, and stratum Malpighii. These layers comprise the epidermis.

Figure 3A:
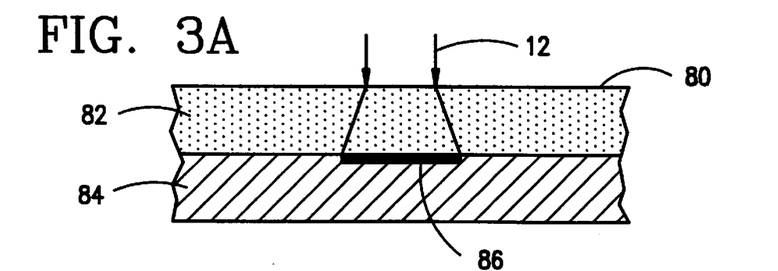
FIG. 3A to FIG. 3E show a time sequence of subsurface skin heating and surface thermal emission.

Beneath the translucent layer 82 lies a blood vessel layer 84 comprising the papillary layer of derma, rete subpapillare, reticular layer of derma, rete cutaneum, and subcutaneous tissue. The papillary and reticular layers contain blood vessels and efficiently absorb the laser light beam 12.

In practice, the laser light beam 12, for example, the laser measurement pulse 50 discussed above, first enters the skin surface 80 and spreads slightly in the translucent layer 82. A blood vessel heating area 86 marks the level at which the energy of the beam 12 is absorbed (see FIG. 3A).

Figure 3B:
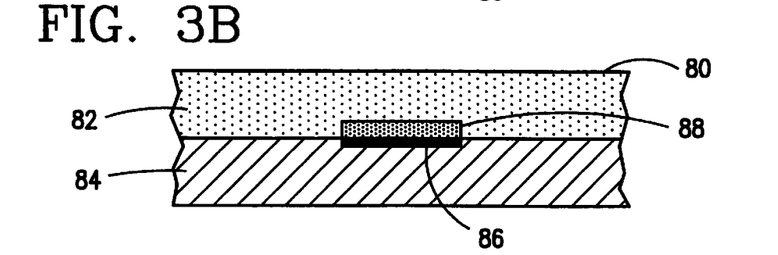

A temperature increase 88 then arises from the heated area 86 (see FIG. 3B). (For clarity, only the temperature increase toward the skin surface 80 is shown.)

Figure 3C:
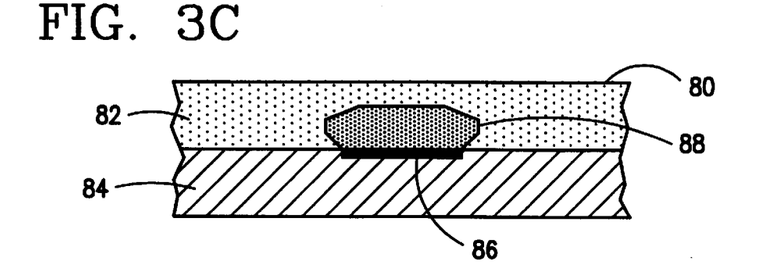

The temperature increase 88 then expands and rises as it propagates toward the skin surface 80 (see FIG. 3C). The temperature increase 88 moves, just reaching the skin surface 80. The temperature increase 88 then expands and intensifies at the skin surface 80, causing a measurement thermal emission 54 to radiate (see FIG. 3E) at some later time, T2, in response to the initial measurement pulse 50.

With reference to FIG. 2, a delay time 52 separates the occurrence of measurement pulse 50 and thermal emission 54. The delay time 52 typically ranges from 1000 to 3000 microseconds.

The thermal emission 54 exhibits an initial rise rate 56. FIG. 2 shows the initial rise rate 56 extended in a straight line to clearly illustrate the rate's slope.

An indefinite time 58 ensues after the thermal emission 54 for calculation, physician approval, and energy adjustment (discussed below in greater detail). After adjustment, the physician or operator initiates a high energy treatment pulse 60 via the control console 40 (see FIG. 1) and a large, treatment thermal emission 62 occurs. The treatment pulse 60 initiates a similar heat response as described above with reference to the measurement pulse 50 and as shown in FIGS. 3A to 3E.

Operation

Where manual control initiates each pulse, the physician or operator first positions the apparatus on the desired skin treatment area. Treatment begins with manual initiation of a measurement pulse 50 from the control console 40 (FIGS. 1 and 2). The control console 40 sets the energy control signal 44 at a known, predetermined low energy. This low energy is preferably below the threshold of coagulation, but above the minimum required by the detector 26 for detecting the measurement thermal emission 54. After the energy control signal 44 is set, the operator activates the control console 40 to initiate the on/off control signal 42 and the laser 10 emits the measurement pulse 50, shown as laser light beam 12.

Referring to FIG. 3A, and as discussed above, the laser light beam 12 enters the skin surface 80. The beam 12 travels very quickly (one billionth of a second) through the translucent layer 82. Since the translucence of the layer 82 diffuses and spreads the beam 12, the beam 12 is preferably as wide as, or wider than, the thickness of the layer 82. When the beam 12 is wide, the width increase due to diffuse spread is small compared to the total beam width.

Upon reaching the blood vessel layer 84, the blood vessels absorb the beam 12, producing the heated area 86. The heated area 86 is much hotter than normal tissue temperature, but preferably well below coagulation or tissue damage temperatures.

The transfer of heat energy from the heated area 86 to the translucent layer 82 involves two physical mechanisms or properties, thermal conduction and heat capacity. The thermal conduction of a medium determines the rate of heat energy transfer for a given temperature difference. A high thermal conductance means a large amount of heat energy flows per time interval for a given temperature difference. The rate at which thermal energy propagates away from the heated area 86 depends, in part, on the thermal conductance of the layer 82.

Heat capacity specifies the energy that must be put into a material to make its temperature rise. For example, one calorie of energy raises the temperature of one gram of water by 1 centigrade degree. Heat energy cannot be transferred by conduction until there is a temperature difference. A temperature difference cannot occur until the stored heat energy increases.

The first heat energy which flows from the heated area 86 into the layer 82 is stored in the layer of adjacent molecules. As this stored energy increases, the temperature of the adjacent molecule layer increases from its initial normal skin temperature.

As the temperature of the adjacent molecules rise, they begin to transfer some of the received energy to the next further molecule layer by conduction. This "leaky-bucket brigade" causes the leading edge of the temperature increase 88 to propagate at a definite, slow speed.

Figure 3D:
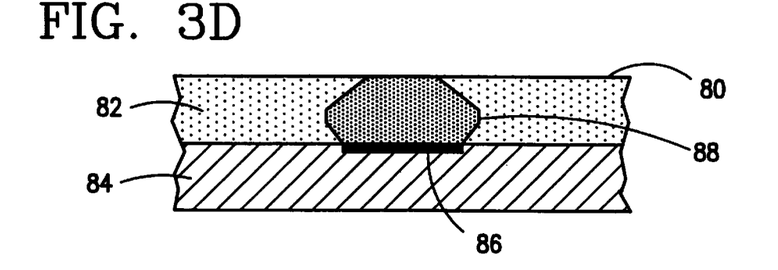

As discussed above, FIG. 3B depicts the temperature increase 88 in a region adjacent to the heated area 86. FIG. 3C shows the temperature increase 88 spreading as it propagates toward the skin surface 80. FIG. 3D shows the spreading temperature increase 88 reaching the skin surface 80. The temperature at the outer edge of the temperature increase 88 is near normal skin temperature, while the temperature at the area 86 is still near the original, laser induced, high temperature.

The time for the temperature increase 88 to propagate to the surface 80 depends on the thickness of the layer 82 and on the ratio of thermal conductivity to thermal capacity. This ratio is commonly known as thermal diffusivity. The thermal diffusivity is nearly constant for epidermis on a given area of the body (e.g., face, leg). Consequently, the time for the temperature increase 88 to reach the surface 80 indirectly measures layer 82 thickness at treatment site 14.

Upon reaching skin surface 80, the temperature increase 88 radiates an electromagnetic energy characteristic of heated bodies. The electromagnetic energy is shown as measurement thermal emission 54 in FIG. 3E.

Figure 3E:
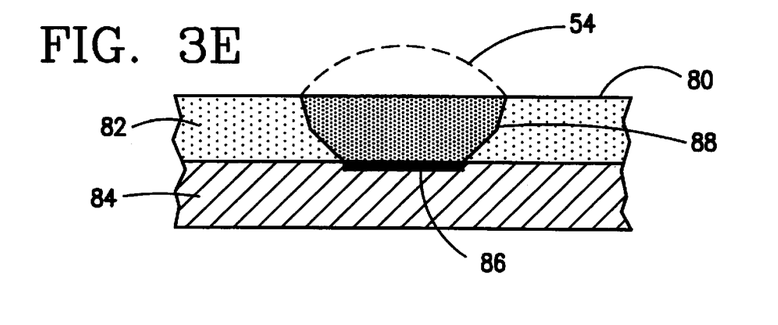

As energy continues to propagate from the heated area 86, the center of the thermal emission 54 becomes hotter and the edges spread further (thus defining the initial rise rate 56). Eventually, the energy of the heated area 86 is spread through the layer 82 and the thermal emission 54 reaches a peak. Further spreading and radiation cools the skin until it eventually returns to normal temperature.

The delay 52 is substantially a function of thermal diffusivity, beam geometry, and layer thickness. Since thermal diffusivity and beam geometry are essentially constant, the scalar time delay is a direct measure of layer thickness. Thus, one scalar measurement quantity is obtained, wherein the measured quantities of the present invention are simple scalars (quantities completely described by a single number) rather than a matrix, vector field, tensor, pixel mapped image, or other complex data combination.

Thermal Emission Processing

Manual operation as discussed above results in a delay 52 (directly providing layer thickness information), measurement thermal emission 54 and initial rise rate 56. In accordance with the present invention, these quantities are then measured and quantified to produce a controlled treatment pulse 60.

With reference to FIG. 1 and time T1 of FIG. 2, diffuse reflection 18 occurs as the measurement pulse 50 enters the treatment site 14. The diffuse reflection 18 propagates, ever spreading, and a portion reaches the concentrator 22. The spectral filter 24 stops the radiant energy from diffuse reflection 18 and the diffuse reflection 18 has no further effect on the operation of the present invention.

Somewhat later, at T2 of FIG. 2, measurement thermal emission 54 occurs. As with diffuse reflection 18, the radiant energy of this emission spreads. The concentrator 22 intercepts a portion, relaying the concentrated energy to the spectral filter 24. The spectral filter 24 passes the concentrated energy with negligible attenuation. The concentrated energy focuses on the infrared detector 26. The infrared detector 26 converts the concentrated radiant energy to an electrical waveform signal 28.

The waveform signal 28 contains only amplitude versus time information. Spatial information is not included or needed. Consequently, the infrared detector 26 can be a single element infrared detector, and a method for predicting an effective and safe laser light energy range is thereby provided wherein the measured quantities can be obtained, if desired, from a simple, single element infrared detector rather than an expensive infrared camera. In accordance with the preferred embodiment of the present invention an Intrel Service Company Model 101B infrared detector is used. The Intrel Service Company Model 101B infrared detector provides an inexpensive, non-cryogenic infrared detector with adequate speed and sensitivity, although those skilled in the art will understand that other detectors may be used without departing from the spirit of the present invention.

The processor 30 measures the time between the on/off control signal 42 and the initial waveform signal 28 from the infrared detector 26. Since the on/off control signal 42 is synchronous with the measurement pulse 50 (FIG. 2), the measured delay 52 spans T1 to T2. The waveform signal 28 subsequent to T2 corresponds to the measurement thermal emission 54.

Upon sensing the initial waveform signal 28, the processor 30 measures the signal amplitude increase over a short time interval following T2. This measurement yields the initial rise rate 56, which is signal amplitude increase divided by time interval.

The initial rise rate 56, is a simple scalar quantity, thereby once again providing a system wherein the measured quantities are simple scalars rather than a matrix, vector field, tensor, pixel mapped image, or other complex data combination. The initial rise rate 56 is the second and last measured quantity needed for subsequent calculations, providing a method wherein the calculations require only 2 simple, scalar measured quantities.

The processor 30 then transfers the measurement results, initial rise rate signal 34 and the delay signal 32, to the computer 36. The computer 36 uses a thickness table of corresponding values. The table would be readily generated by a manufacturer for specific skin types using physical algorithms well known to those of ordinary skill in the art to associate the thickness of the layer 82 with the measured delay signal 32.

The deduced thickness of the layer 82 (FIG. 3A) and measured rise rate signal 32 (see FIG. 1), in conjunction with a temperature table, allow the computer 36 to deduce the initial temperature of the heated area 86 (FIG. 3A). As with the thickness table, this table would be readily generated by a manufacturer based upon beam diameter, beam energy, laser wavelength and focus geometry using physical algorithms well known to those of ordinary skill in the art.

Both the thickness table and temperature table are pre-computed. They come from well known heat transfer formulae, from empirical measurements, or from a combination of analytical and empirical sources.

The temperature threshold for coagulation and for skin damage are known from existing research. As such, the computer 36 calculates two ratios, one for the temperature threshold for coagulation and one for the temperature threshold for skin damage.

The computer 36 divides the known coagulation temperature by the deduced temperature of the heated area 86 to produce the coagulation temperature ratio. The computer 36 then multiplies (scales) the known energy of the measurement pulse 50 by the coagulation temperature ratio. The result is the minimum energy for coagulation.

A similar calculation yields the maximum allowed laser beam energy. The computer 36 divides the skin damage threshold temperature by the deduced temperature of the heated area 86 to produce the skin damage temperature ratio. The computer 36 then multiplies the energy of the measurement pulse 50 by this second ratio. The result is the maximum energy which does not cause skin damage.

The energy bounds calculation is now complete. The bounds extend from the lowest energy that will coagulate (minimum effective energy) to the maximum energy below the skin damage threshold (maximum safe energy). These bounds provide a method for predicting an effective and safe laser light energy range, wherein calculations based on measured quantities advise the physician of the energy bounds for safe and effective treatment.

Look up tables and ratio scaling are sufficient to calculate the energy bounds. These simple operations are within the capability of most, if not all small, inexpensive microprocessors. In contrast, and as discussed in the Background of the Invention, calculations for CAT images, tensors, bit fields, and matrices require many more computations, each being of a more complex nature. Thus, the present method provides a system wherein the energy bounds come from algorithms and formulae much simpler than those required for CAT images, allowing fast processing on computers of modest computing power.

A single, larger table provides an alternative to two ratio calculations and two tables discussed above. The single table is normalized to the measurement pulse 50 energy. The single larger table is two dimensional, being accessed directly by measured values of the delay 52 and the rise rate 56. At each accessed location of the table lie two values, one for the minimum laser energy and one for the maximum laser energy. The single table eliminates ratio calculations and scaling, but requires considerably more storage space.

Typically, the maximum energy allowed before damage is greater than the minimum energy required to coagulate. If this is not true at a particular site, the site cannot be treated without skin damage. The physician may choose to skip the site or to treat it anyway.

Physician or Operator Interaction

After the bounds computation is completed, the computer 36 transfers the maximum and minimum energy settings to the control console 40. These settings determine the safe energy range for the treatment pulse 60.

The control console 40, in manual operation, preferably displays the safe energy range for the physician. The physician sets the laser energy within the allowed range according to judgement factors gained through experience. When constrained to this range, the physician's choice will be both effective and safe.

Referring to FIG. 2, the physician may spend indefinite time 58 setting the energy. When set, the physician initiates the treatment pulse 60, indicated at T3.

The treatment pulse 60 contains considerably more energy than the measurement pulse 50. The energy may be increased by increasing the pulse intensity (height), "on" duration (width), or both (as shown).

The present apparatus makes no further measurements or pulses at this treatment site. However, the treatment thermal emission 62 will well up some milliseconds later at T4, caused by the treatment pulse 60.

The operation of the present predictive beam energy controller apparatus is now finished at the treatment site 14.

Figure 4:
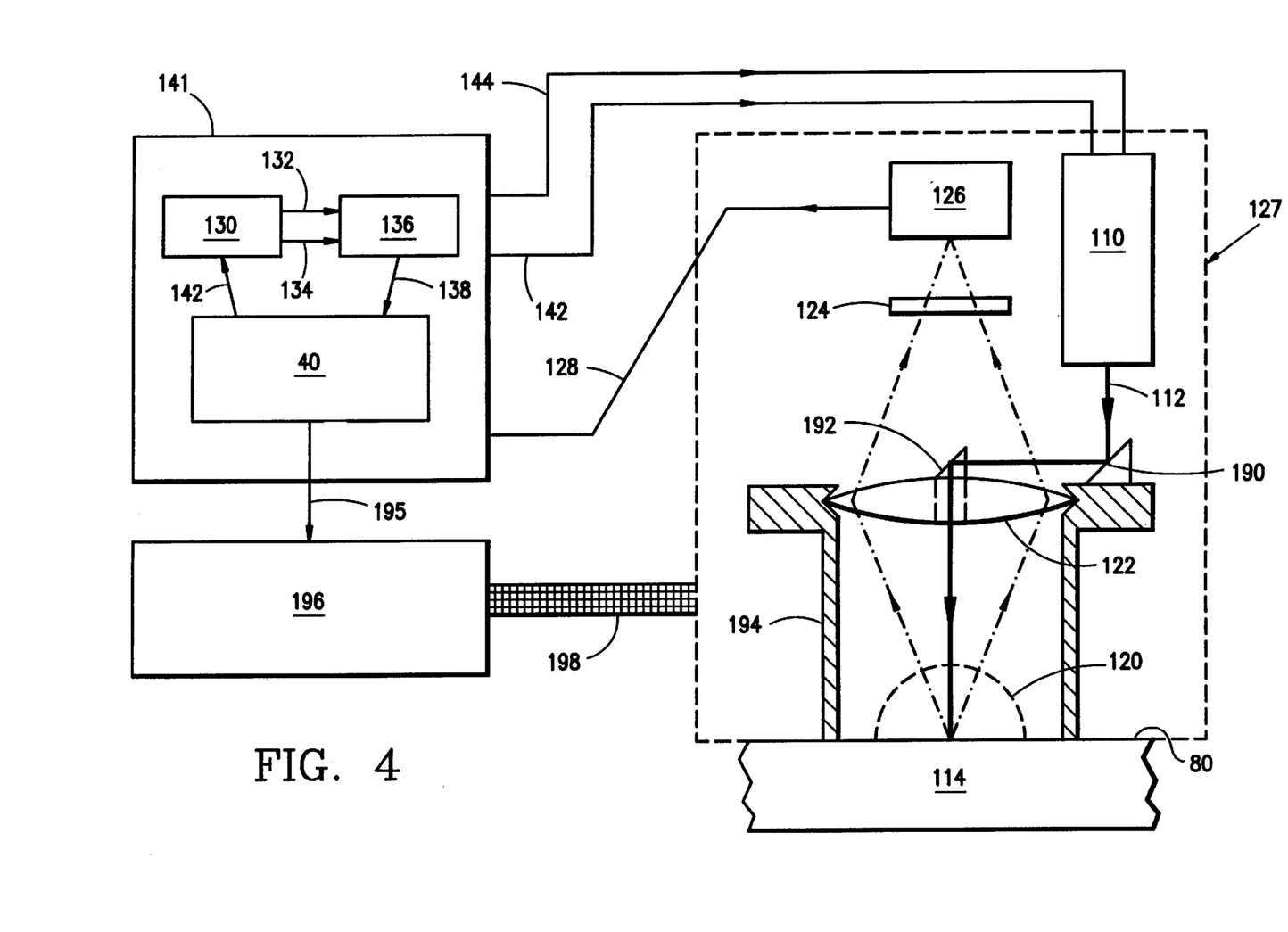
FIG. 4 is a schematic of a preferred embodiment of the present invention.

With reference of FIG. 4, an alternate embodiment of the present predictive beam energy controller is disclosed. In accordance with this embodiment, the laser and thermal emission paths are coaxially aligned. Coaxial alignment results in more efficient collection of energy from thermal emission 54, allowing a lower energy measurement pulse.

The laser 110 produces a beam 112 which reflects off a first mirror 190. The beam 112 then reflects off a second mirror 192 (typically a total internal reflection prism) and passes through a hole in the concentrator 122. The beam 112 then travels to the treatment site 114. The beam 112 is preferably collimated, retaining approximately the same diameter along its travel path.

The concentrator 122 contains a small central hole which passes the beam 112 without attenuation. The concentrator 122 focuses radiant energy from the treatment site 114 onto the detector 126. The spectral filter 124 prevents scattered and reflected laser light from reaching the infrared detector 126. As discussed above with regard to the embodiment disclosed in FIG. 1, the spectral filter 124 is typically an inherent property of the concentrator 122, the detector 126, or both, although other techniques may be employed without departing from the spirit of the present invention.

A transparent housing 194 spaces the apparatus a proper distance from the skin surface 180, such that the concentrator 122 is most effective. Typically, this spacing focuses an image of site 114 on the detector 126. Being transparent, the housing 194 allows the physician to position and to monitor the treatment area.

The controller includes an optical assembly 127 comprising the laser 110, the concentrator 122, the filter 124, the detector 126, the first mirror 190, the second mirror 192, and the housing 194. This group of components typically have fixed relative positions.

Three signals pass from the optical assembly 127 to the signal processor assembly 141: a waveform signal 128, an on/off signal 142, and an energy control signal 144.

It is envisioned that some embodiments of the optical assembly will be small, pencil or wand shaped assemblies that are maneuvered by the physician like a scalpel. It is also envisioned that more efficient and less costly embodiments of the optical assembly will be too large or heavy for easy manual positioning.

Where the positioning servomechanism 196 assists in moving the optical assembly 127 to a treatment site 114, the servomechanism 196 attaches to the assembly 127 through a conventional mechanical connection 198. Communicating device, interface device, or control console 140, part of the signal processor assembly 141, issues control commands to the servomechanism 196.

Manual operation of the embodiment disclosed in FIG. 4 begins with the physician or operator guiding the optical assembly 127 to the skin area to be treated. Where the optical assembly 127 is small and light, positioning is accomplished by hand movement.

For heavier and larger embodiments, the servomechanism 196 aids in positioning the assembly 127. One envisioned control for servomechanism 196 uses a conventional joystick or similar positioning control. Another envisioned control for the servomechanism 196 works like conventional power steering or power brakes in an automobile. Control of the servomechanism 196 comes from sensing a manually applied positioning force, where typically 90% of the lifting or traversing force is provided by the servomechanism 196.

It is further envisioned that the visible laser beam 112, typically yellow in color, serves as a beacon to mark the exact targeted treatment area. The laser beam 112 is set at a low energy, preferably lower than the measurement pulse 50 yet high enough to make diffuse reflection 118 clearly visible. Acting as a beacon, the laser beam 112 illuminates the treatment site 114 with a yellow flash of light, typically at one second intervals. The location of the reflection 118 guides the physician in accurately positioning treatment site 114.

Once positioned, the present predictive beam energy controller operates as previously described.

A predictive beam energy controller such as the embodiment disclosed in FIG. 4, may incorporate a semiautomatic operating mode. In semiautomatic operation, the optical assembly 127 is automatically moved from site to site by the servomechanism 196. The semiautomatic operation treats large areas of skin quickly, uniformly, and accurately.

Typically, where manual treatment is performed, the treatment site will have an area of 4 square millimeters, whereas a semiautomatic treatment may cover 400 square millimeters or more. Since an estimated time for semiautomatic treatment at one site is on the order of 10 milliseconds, 400 square millimeters can be treated in one second. Manual operation takes an estimated 20 seconds per site, making semiautomatic operation 2000 times faster. Therein lies the advantage of semiautomatic operation.

Referring again to FIGS. 2 and 4, in semiautomatic operation, the physician first selects a treatment area rather than a specific site. The chosen area should have nearly uniform skin characteristics. Next, using the control console 140, the physician sets the energy level for all sites in the treatment area, preferably by specifying a fraction of the allowed energy range, typically 50%. The physician or operator then initiates semiautomatic operation using the control console 140.

Semiautomatic operation proceeds as follows. The control console 40 automatically initiates the measurement pulse 50 at a treatment site. When the energy range signal 138 arrives from the computer 136, the console 140 sets the energy control signal 144 to the prescribed fraction (e.g., 50%). The console 140 then automatically initiates the treatment pulse 60.

Upon completing the treatment pulse 60, the control console 140 preferably does not wait for treatment thermal emission 62 to subside. Instead, the control console 140 activates the positioning servomechanism 196 to quickly move the treatment site 114 to a non-adjacent area. By moving to a non-adjacent site, the treatment thermal emission 62 will not interfere with the new measurement thermal emission 54. The semiautomatic pulse sequence then repeats immediately at the new site 114.

The control console 140 repeats the movement and pulsing sequence until all sites in the semiautomatic treatment area are treated. The control console 140 then reverts to manual control. The control console 140 typically includes a feature to manually terminate semiautomatic operation.

While various preferred embodiments have been shown and described, it will be understood that there is no intent to limit the invention by such disclosure, but rather, is intended to cover all modifications and alternate constructions falling within the spirit and scope of the invention as defined in the appended claims.

What is claimed is:

1. A method for predicting an effective and safe laser light energy range for sub-epidermal laser surgery, comprising the steps of:
   impinging a measurement laser pulse on a treatment area, the pulse having an energy below a predetermined threshold of coagulation and below a predetermined threshold of skin damage;
   detecting a thermal emission caused by the measurement laser pulse emanating from the treatment area;
   measuring a delay time from the measurement laser pulse to the detection of the thermal emission;
   measuring a rise rate of the thermal emission;
   calculating a layer thickness based upon the delay time, wherein the thickness is substantially the epidermal thickness;
   calculating an internal measurement temperature rise based upon the layer thickness and the rise rate;
   multiplying the energy of the measurement laser pulse by a minimum scaling ratio to obtain a minimum laser treatment energy, wherein the minimum scaling ratio is the known coagulation temperature divided by the measurement temperature rise; and
   multiplying the energy of the measurement laser pulse by a maximum scaling ratio to obtain a maximum laser treatment energy, the maximum scaling ratio is the known skin damage threshold temperature divided by the measurement temperature rise.

2. The method as set forth in claim 1, wherein the results of steps of calculating and multiplying are obtained from a pre-computed, normalized, two dimensional table, the table being indexed by the delay time and the rise rate, and the table having a value for minimum laser treatment energy and maximum laser treatment energy at each indexed location.

3. The method as set forth in claim 1, wherein the duration of the measurement laser pulse is less than approximately 500 microseconds.

4. The method as set forth in claim 1, wherein the measurement laser pulse has a yellow hue allowing identification of the treatment site prior to impinging the measurement laser pulse at the predetermined treatment site.

5. An apparatus which computes an energy range extending from a minimum energy to coagulate to a maximum energy which does not cause skin damage for sub-epidermal laser surgery, the apparatus comprising:
   a laser for delivering a measurement laser pulse to the skin treatment site, the measurement laser pulse having an energy below a predetermined threshold of coagulation and below a predetermined threshold of skin damage, and the laser having a switching means for turning the beam on and off;
   means for detecting a thermal emission caused by the measurement laser pulse emanating from the treatment area;
   means for measuring a delay time from the measurement laser pulse to detection of the thermal emission;
   means for measuring the rise rate of the thermal emission; and
   computing means for calculating, based upon the delay time and from the rise rate, a minimum laser treatment energy sufficient to coagulate and a maximum laser treatment energy below the threshold of skin damage.

6. The apparatus as set forth in claim 5, wherein the means for detecting the thermal emission includes a single element infrared detector.

7. The apparatus as set forth in claim 5, wherein the laser is associated with a control console capable of selectively providing energy levels required for both measurement laser pulses and treatment laser pulses.

8. The apparatus as set forth in claim 7, wherein the control console extends to sufficiently low energy levels to allow the laser beam to be used as a treatment site marker.

9. The apparatus as set forth in claim 7, wherein the control console activates the switching means, initiating the measurement pulse and the treatment pulse in response to commands from a human operator.

10. The apparatus as set forth in claim 7, further including a positioning means for selectively moving the laser.

11. The apparatus as set forth in claim 10, wherein the control console activates the switching means, and steers the positioning means, thereby automatically initiating pulses to measure and treat an area of skin comprised of multiple treatment sites.

12. The apparatus as set forth in claim 10, wherein the positioning means moves to successive non-adjacent treatment sites as it covers a predetermined area of skin.

13. The apparatus as set forth in claim 5, further including means for a human interface displaying the minimum laser treatment energy and the maximum laser treatment energy for consideration by individuals performing the procedure.

14. The apparatus as set forth in claim 5, wherein the apparatus includes means for semiautomatic operation.

15. The apparatus as set forth in claim 5, where laser beams issued by the laser are coaxially aligned with the means for detecting the thermal emission.

* * * * *